United States Patent [19]

Hadley et al.

[11] Patent Number: 4,988,706
[45] Date of Patent: Jan. 29, 1991

[54] CERTAIN PHARMACEUTICALLY USEFUL OXADIAZOLES

[75] Inventors: Michael S. Hadley; Barry S. Orlek; Paul A. Wyman; Harry J. Wadsworth, all of Harlow, England

[73] Assignee: Beecham Group P.L.C., Middlesex, England

[21] Appl. No.: 337,282

[22] Filed: Apr. 13, 1989

[30] Foreign Application Priority Data

Apr. 15, 1988 [GB] United Kingdom ............... 8808926

[51] Int. Cl.$^5$ .................. A61K 31/44; C07D 471/08
[52] U.S. Cl. ............................. 514/299; 514/214; 514/364; 540/582; 546/112; 548/131; 548/132; 548/133; 548/143; 548/144
[58] Field of Search ............... 546/112; 548/131, 132, 548/133, 143, 144; 540/582; 514/214, 299, 364

[56] References Cited

U.S. PATENT DOCUMENTS 4,771,051 9/1988 Wätjen et al. ............... 548/131
4,797,387 1/1989 King ......................... 514/212

FOREIGN PATENT DOCUMENTS 0239309 9/1987 European Pat. Off. .
0301729 2/1989 European Pat. Off. .

OTHER PUBLICATIONS

Eckhardt et al., Chem. Abstracts, vol, 78, 84203q (1973).

Primary Examiner—Mary C. Lee
Assistant Examiner—Bernard I. Dentz
Attorney, Agent, or Firm—Hopgood, Calimafde, Kalil, Blaustein & Judlowe

[57] ABSTRACT

Novel compounds of formula (I), processes for their preparation, and their use as pharmaceutical agents are described:

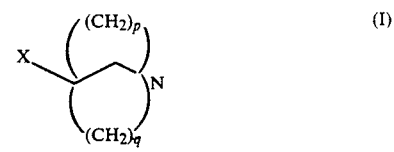

in which X represents a group

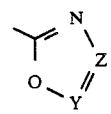

wherein one of Y and Z represents nitrogen and the other represents CR where R is selected from halogen, CN, $OR^1$, $SR^1$, $N(R^1)_2$, $NHR^1$, $NHCOR^1$, $NHCOOCH_3$, $NHCOOC_2H_5$, $NHOR^1$, $NHNH_2$, $COR^1$, $COR^2$, $C_{2-4}$ alkenyl, $C_{2-4}$ alkynyl or $C_{1-2}$ alkyl substituted with $OR^1$, $N(R^1)_2$, $SR^1$, $CO_2R^1$, $CON(R^1)_2$ or one or two halogen atoms, in which $R^1$ is hydrogen or $C_{1-2}$ alkyl and $R^2$ is $OR^1$, $NH_2$ or $NHR^1$; and each of p and q independently represents an integer of 2 to 4.

7 Claims, No Drawings

CERTAIN PHARMACEUTICALLY USEFUL OXADIAZOLES

This invention relates to compounds having pharmaceutical activity, to a process for their preparation and their use as pharmaceuticals. EP-A No. 0239309 (Merck Sharp and Dohme Ltd.) discloses substituted oxadiazoles which are muscarinic agonists. A novel group of compounds has now been discovered which also enhance acetylcholine function via an action at muscarinic receptors within the central nervous system and are therefore of potential use in the treatment and/or prophylaxis of dementia in mammals. According to the present invention, there is provided a compound of formula (I) or a pharmaceutically acceptable salt thereof:

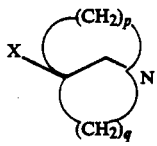

in which X represents a group

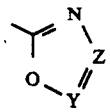

wherein one of Y and Z represents nitrogen and the other represents CR where R is selected from halogen, CN, $OR^1$, $SR^1$, $N(R^1)_2$, $NHR^1$, $NHCOOCH_3$, $NHCOOC_2H_5$, $NHOR^1$, $NHNH_2$, $COR^1$, $COR^2$, $C_{2-4}$ alkenyl, $C_{2-4}$ alkynyl or $C_{1-2}$ alkyl substituted with $OR^1$, $N(R^1)_2$, $SR^1$, $CO_2R^1$, $CON(R^1)_2$ or one or two halogen atoms, in which $R^1$ is hydrogen or $C_{1-2}$ alkyl and $R^2$ is $OR^1$, $NH_2$ or $NHR^1$; and each of p and q independently represents an integer of 2 to 4.

The term halogen includes bromine, chlorine and fluorine.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferably, p and q each independently represents 2 or 3. Most preferably p represents 2 and q represents 2 or 3.

Preferably, R is selected from $NH_2$, $CH_2F$ and $NHCOCH_3$. Suitable examples of X include 3-fluoromethyl-1,2,4-oxadiazol-5-yl, 3-amino-1,2,4-oxadiazol-5-yl and 3-acetylamino-1,2,4-oxadiazol-5-yl.

The invention also provides a process for the preparation of a compound of formula (I), or a pharmaceutically acceptable salt thereof, which process comprises cyclising a compound of formula (II):

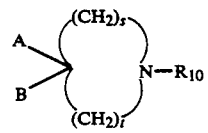

in which (i) A represents X or a group convertible thereto and B represents $-(CH_2)_rL_1$ where $L_1$ is a leaving group or A and $L_1$ together represent $-COO-$; one of r, s and t is 1 and the other two independently represent an integer of 2 to 4, and $R_{10}$ represents hydrogen or an N-protecting group; to give a compound of formula (IIa):

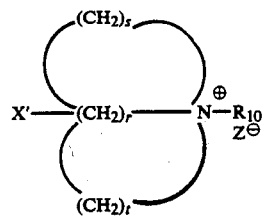

in which X' represents X or a group convertible thereto, $Z^\ominus$ is an anion and the remaining variables are as previously defined; or (ii) A represents an electron withdrawing group, B represents hydrogen and $R^{10}$ represents $-(CH_2)_rL_2$ where $L_2$ is a leaving group; one of s and t is 1 and the other and r independently represent an integer of 2 to 4; to give a compound of formula (IIb):

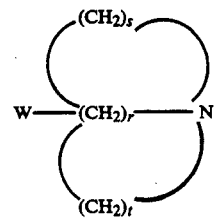

in which W represents an electron withdrawing group or X and the remaining variables are as previously defined; and thereafter, optionally or as necessary, removing any $R_{10}$ N-protecting group, converting W to X., converting X to X, converting X to other X and/or forming a pharmaceutically acceptable salt.

The deprotection, conversion and interconversion steps may be carried out in any appropriate order.

Examples of the leaving groups $L_1$ and $L_2$ include halo such as bromo or chloro, tosyloxy and mesyloxy.

Examples of $R_{10}$ when an N-protecting group include benzyl and substituted benzyl.

Examples of A and X. when groups convertible to X include $C_{1-4}$ alkoxycarbonyl, benzyloxycarbonyl and cyano.

The cyclisation reaction is a nucleophilic substitution which may be carried out under conventional conditions appropriate to the groups A and B. Thus, when B is $(CH_2)_rBr$ and A is $C_{1-4}$ alkoxycarbonyl, the cyclisation is carried out in an inert solvent such as toluene or ether at elevated temperature. When B is $(CH_2)_rOTos$ or $(CH_2)_rOMes$, it is preferably obtained by treatment of a $(CH_2)_rOH$ group with a suitable reagent such as tosyl chloride or mesyl chloride, in a base such as pyridine, whereupon the cyclisation may proceed at ambient temperature, or at elevated temperature in an inert solvent such as toluene. When A and $L_1$ together represent —COO—, the cyclisation may be carried out in a lower alkanol such as ethanol in the presence of acid such as hydrogen bromide. In the resulting compound of formula (IIa), X will be an alkoxycarbonyl group corresponding to the lower alkanol used for the cyclisation.

Where $R_{10}$ is an N-protecting group such as benzyl, this may be removed by conventional hydrogenation, preferably catalytically over a suitable catalyst such as Pd/C. Examples of A when an electron withdrawing group include $C_{1-4}$ alkoxycarbonyl and cyano.

When A is an electron withdrawing group such as $C_{1-4}$ alkoxycarbonyl, B is hydrogen and $R^{10}$ is -$(CH_2)_rL_2$ where $L_2$ is, for example, chloro, the cyclisation may be effected by treatment of the compound of formula (II) with lithium diisopropylamide.

The conversion of W and X' may be carried out conventionally with regard to the group X.

Thus, the group X may be obtained from a W or X' group as described in, for example standard text books on heterocyclic chemistry such as 'Comprehensive Heterocyclic Chemistry', A. R. Katritzky and C. W. Rees, Pergamon, 1984.

The W or X' group is first converted, as necessary, to a suitable starting group X" for the chosen conversion reaction to give the required group X.

An X" carboxy group may be obtained by conventional de-esterification of an X or W alkoxycarbonyl group. Where $R^{10}$ is an N-protecting group and X' or W is a benzyloxycarbonyl group, the de-esterification and deprotection steps may conveniently be effected simultaneously by conventional hydrogenation such as described above. Alternatively, an X' carboxy group may be obtained by conventional acid hydrolysis of an X' or W cyano group.

An X" chlorocarbonyl group may be obtained by treatment of an X" carboxy group with thionyl chloride at elevated temperature.

When X represents 3-substituted-1,2,4-oxadiazol-5-yl, an X" chlorocarbonyl or X' carboxy ester group may be reacted with an appropriate amide oxime, at elevated temperature in an inert, polar solvent such as chloroform, and the resulting substitution product cyclised at elevated temperature in a suitable solvent such as toluene or xylene.

When X represents 3-amino-1,2,4-oxadiazol-5-yl, an X" chlorocarbonyl or X' carboxy ester group may be reacted with a hydroxy guanidine derivative under basic conditions.

When X represents 5-substituted-1,3,4-oxadiazol-2-yl, an X" carboxy or carboxy ester group may be converted to the acid hydrazide by conventional procedures. For 5 example, the acid may be converted to a $C_{1-6}$ alkyl 6 ester e.g. methyl, with the appropriate $C_{1-6}$ alkanol e.g. methanol under conventional esterification conditions, and the resulting ester reacted with hydrazine at elevated temperature to give the acid hydrazide. The acid hydrazide may then be acylated with an appropriate agent such as the anhydride and then cyclised by heating with phosphorus oxychloride or polyphosphoric acid, or methane sulphonic acid in the presence of phosphorus pentoxide.

Interconversion of R within a group X may be carried out conventionally. Thus, an amino group may be acylated, converted to chloro, or to —NHNH$_2$ via a diazonium intermediate, —N$_2^+$. Similarly, a chloro substituent may be converted by reaction with a nucleophile such as methoxide; and alkoxycarbonyl groups may be converted, via carboxy, to an amino substituent —NH$_2$.

Compounds of formula (II) may be prepared conventionally.

Where A is $C_{1-4}$ alkoxycarbonyl, B is $(CH_2)_rL_1$ and $R_{10}$ is hydrogen or an N-protecting group, the compound of formula (II) may be prepared by treating a compound of formula (III):

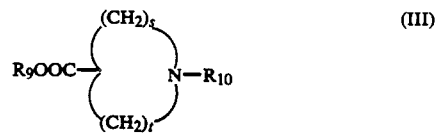

where $R^9$ is $C_{1-4}$ alkyl and the remaining variables are as previously defined, with lithium diisopropylamide, prepared in situ from diisopropylamine and n-butyllithium followed by reaction with a compound $L_3(CH_2)_rL_1$ where $L_3$ is a leaving group, in an inert solvent such as ether at depressed to elevated temperature. Both $L_1$ and $L_3$ are suitably bromo.

Where A and $L_1$ together represent —COO— and r is 2, the compound of formula (II) may be prepared by reacting the compound of formula (III), treated with lithium diisopropylamide as before, with ethylene oxide in an inert solvent such as ether at depressed to elevated temperature.

Where A is an electron withdrawing group such as $C_{1-4}$ alkoxycarbonyl, B is hydrogen and $R_{10}$ is $(CH_2)_rL_2$, the compound of formula (II) may be prepared by reacting the compound of formula (III) where $R_{10}$ is hydrogen with a compound $L_3(CH_2)_rL_2$ where $L_3$ is as previously defined, in a solvent such as acetone in the presence of a base such as potassium carbonate. The leaving group $L_3$ is preferably bromo and $L_2$ is preferably chloro.

Compounds of formula (III) are known compounds or may be prepared by analogous methods to those for preparing known compounds. The compound of formula (III) where s is 2 and t is 1 and $R_{10}$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with BH$_3$ in tetrahydrofuran, at ambient to elevated temperature.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

Fluoroacetamide Oxime (D1)

A solution of sodium methoxide (prepared from 1.84g, 0.080 mole of sodium) in methanol (40ml) was added to a solution of hydroxylamine hydrochloride (5 56g, 0.080 mole) in methanol (40ml) and the mixture stirred for 20 minutes. The mixture was filtered through a pad of kieselguhr and the filtrate cooled to 0° C. and treated with fluoroacetonitrile (5.0g, 0.085 mole). The solution was allowed to warm up to room temperature over 1h and then concentrated in vacuo. The residue was treated with methanol (15ml)/chloroform (120ml), filtered and the filtrate concentrated in vacuo to give the title compound (D1) as a white solid (6.8g, 92%) m.p. 41°–43° C.

DESCRIPTION 2

(±) Ethyl 1-(2-chloroethyl)-3-piperidylcarboxylate (D2)

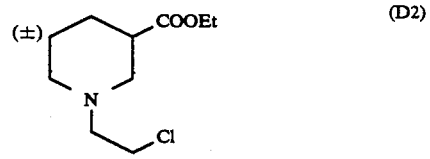

A solution of ethyl 3-piperidylcarboxylate (100g, 0.64 mole) in acetone (600ml) was treated with 1-bromo-2-chloroethane (54ml, 0.64 mole) and anhydrous potassium carbonate (138g, 1.00 mole) and the mixture stirred at room temperature for 24h. The mixture was concentrated in vacuo and the residue treated with water (400ml) and extracted with ether (2×200 ml). The combined ether extracts were dried (Na₂SO₄) and concentrated in vacuo to leave a yellow oil, which was purified by chromatography on silica gel eluting with 50% ether/60-80 petrol to give the title compound (D2) as a pale yellow oil (50.0g, 36%). ¹H Nmr (CDCl₃)δ1.25 (3H, t, J=7Hz), 1.40-3.10 (11H, m), 3.58 (2H, t, J TM 7Hz), 4.15 (2H, q, J=7Hz)

DESCRIPTION 3

(±) Ethyl 1-azabicyclo[3.2.1]Oct-5-ylcarboxylate (D3)

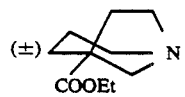

A solution of diisopropylamine (33.6ml, 0.24 mole) in dry ether (1500ml) at −65° C. under nitrogen was treated with 1.5M n-butyllithium in hexane (150ml, 0.225 mole) and the solution stirred for 15 mins, before adding N,N,N',N'-tetramethylethylenediamine (68ml, 0.45 mole). After stirring for a further 15 mins, the solution was treated with a solution of (±) ethyl 1-(2-chloroethyl)-3-piperidylcarboxylate (D2, 44.7 g, 0.204 mole) in dry ether (100ml) and the mixture allowed to warm up to room temperature over 2 h. The reaction mixture was treated with potassium carbonate solution (300ml) and the ether layer separated, dried (Na₂SO₄) and concentrated in vacuo to leave an orange oil. This was purified by chromatography on silica gel eluting with 10% methanol/chloroform to give the title compound (D3) as a yellow oil (31.9g, 84%), b.p. 120°-130° C.₀.₄mm (Kugelröhr apparatus). ¹H Nmr (CDCl₃)δ1.25 (3H, t, J TM 7Hz), 1.10-2.20 (6H, m), 2.60-3.25 (6H, m), 4.20 (2H, q, J TM 7Hz)

DESCRIPTION 4

(±) Methyl 1-benzyl-2-oxo-4-pyrrolidylcarboxylate (D4)

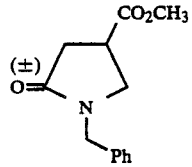

A solution of dimethyl itaconate (50g, 0.32mole) in methanol (40ml) was treated with benzylamine (34.6ml, 0.32mole) and the mixture heated under reflux for 2.5 h. The solution was then concentrated in vacuo and the residue purified by distillation (b.p. 162°-170° C./0.2 mmHg) to give a pale yellow oil. This solidified on standing to give the title compound (D4) as a beige solid (66.2g, 89%), m.p. 62°-63° C.

DESCRIPTION 5

(±) Methyl 1-benzyl-3-pyrrolidylcarboxylate (D5)

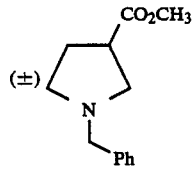

A solution of (±) methyl 1-benzyl-2-oxo-4-pyrrolidylcarboxylate (D4, 35.4g, 0.18 mole) in dry THF (135 ml) was added dropwise over 30 mins to 1M borane-THF solution (228 ml, 0.23 mole) at 0° C. under nitrogen, and when addition was complete the solution was heated under reflux for 1h. The solution was cooled to room temperature, then treated dropwise with 8% hydrogen chloride/methanol (114 ml, 0.25 mole HCl) and stirred for 18 h, followed by 3 h at reflux. The mixture was then concentrated in vacuo and the residue treated with 3 water (40 ml), washed with ether (2×50 ml), basified with 40% sodium hydroxide solution, saturated with potassium carbonate and extracted with ether (3×70 ml). The combined extracts were dried (Na₂SO₄) and concentrated in vacuo to leave a yellow oil, which was purified by distillation (b.p. 146° C./0.7 mmHg) to give the title compound (D5) as a colourless oil (19.8g, 50%).

DESCRIPTION 6

(±) 7-Benzyl-7-aza-2-oxaspiro[4.4]nonan-1-one (D6)

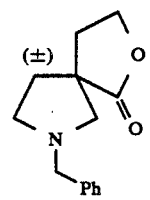

A solution of diisopropylamine (6.6 ml 0.047 mole) in dry ether (100 ml) at −65° C. under nitrogen was treated with 1.6M n-butyllithium in hexane (26.2 ml, 0.042 mole) and the solution stirred for 15 min, before treating with N,N,N',N'-tetramethylethylenediamine 12.3 ml). After stirring for a further 10 min, the solution was treated dropwise over 10 min with a solution of (±) methyl 1-benzyl-3-pyrrolidylcarboxylate (D5, 7.50 g, 0.034 mole) in dry ether (20 ml) and stirring continued at −65° C. for 15 min. Ethylene oxide (3.1 g, 0.070 mole) was then bubbled into the solution over 20 min and the mixture was allowed to warm to room temperature over 2 h followed by 40 min at reflux. The reaction mixture was treated with saturated sodium hydrogen carbonate solution (50 ml) and extracted with ether (3×100 ml). The combined extracts were dried (Na₂SO₄) and concentrated in vacuo to leave an orange oil. The unreacted starting material was removed by heating under reflux in 8M hydrochloric acid (50 ml) for 2 h, followed by basifying to saturation with sodium hydrogen carbonate and extraction with ether. The organic extract was dried (Na₂SO₄) and concentrated in vacuo to leave an orange oil, which was distilled in a Kugelröhr apparatus (b.p. 190°-210° C./0.2-0.5 mmHg) followed by column chromatography on silica gel eluting with ether, to give the title compound (D6) as a pale yellow oil (2.50 g, 36%).

DESCRIPTION 7

Ethyl 1-benzyl-1-azoniabicyclo[2.2.1]hept-4-yl-carboxylate bromide (D7)

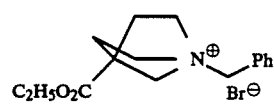

(±) 7-Benzyl-7-aza-2-oxaspiro[4,4]nonan-1-one (D6, 2.5 g, 0.012 mole) was treated with a saturated solution of hydrogen bromide in ethanol (150 ml) and the resulting solution allowed to stand at room temperature for 3.5 days. The solution was concentrated in vacuo and the residue basified with saturated potassium carbonate solution, stirred for 10 mins and then extracted with chloroform (3×50 ml). The combined extracts were dried (Na$_2$SO$_4$) and concentrated in vacuo to give the title compound (D7) as a beige solid (3.40 g, 87%).

DESCRIPTION 8

Ethyl 1-azabicyclo[2.2.1]hept-4-yl-carboxylate (D8)

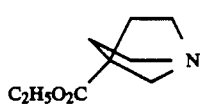

(D8)

Ethyl 1-benzyl-1-azoniabicyclo[2.2.1]hept-4-yl-carboxylate bromide (D7, 15 g, 0.044 mole) in ethanol (250 ml) was hydrogenated over 10% Pd on carbon (1 g). The reaction was then filtered through celite and the filtrate concentrated in vacuo to yield the crystalline hydrobromide. The salt was partitioned between chloroform and saturated aqueous potassium carbonate solution. The organic phase was separated, dried, concentrated in vacuo and distilled to give the title compound (D8) as a colourless oil (7.7 g, 68%), b.p. 203°–205° C./10 mmHg.

EXAMPLE 1

(±) 5-(3-Fluoromethyl-1,2,4-oxadiazol-5-yl)-1azabicyclo[3.2.1]octane oxalate salt (E1)

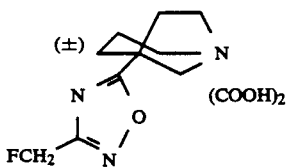

(E1)

A solution of (±) ethyl 1-azabicyclo[3.2.1]oct-5-yl-(-carboxylate (D3, 2.0 g, 0.011 mole) in 8M hydrochloric acid (70 ml) was heated under reflux for 22 h, then concentrated in vacuo to leave a white solid. This was treated with thionyl chloride (30 ml) and heated under reflux for 2.5 h, then concentrated in vacuo to give a yellow solid, which was dissolved in absolute chloroform (100 ml) and treated with fluoroacetamide oxime (D1, 1.1 g, 0.012 mole). The mixture was heated under reflux for 1h, allowed to cool, then treated with excess saturated potassium carbonate solution and extracted with chloroform (2×100 ml). The combined extracts were dried (Na$_2$SO$_4$) and concentrated in vacuo to give a beige solid, which was suspended in dry toluene (100 ml) and heated under reflux for 30 minutes. The mixture was allowed to cool, then filtered and concentrated in vacuo. The residue was chromatographed on silica gel eluting with 0 to 10% methanol/chloroform to give a pale yellow oil, which was converted to its oxalate salt and recrystallised from methanol/ether to give the title compound (E1) as a white solid (290 mg, 9%) m.p. 110°–1130° C.

Oxalate:- $^1$H—NMR (d$_6$—DMSO)δ1.80–1.95 (1H, m), 2.00–2.20 (3H, m), 2.30–2.50 (2H, m), 3.15–3.30 (2H, m), 3.35–3.65 (4H, m), 5.63 (2H, d, J=46Hz)

Analysis - C$_{10}$H$_{14}$N$_3$OF.C$_2$H$_2$O$_4$ requires C: 47.B5. H: 5.35, N: 13.95; found C: 47.95, H: 5.45, N: 13.85

EXAMPLE 2

(±) 5-(3-Amino-1,2,4-oxadiazol-5-yl)-1-azabicyclo[3.2.1]octane (E2)

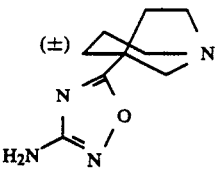

(E2)

To a solution of sodium (3.5 g, 0.15 mole) in anhydrous ethanol (300 ml) under an atmosphere of nitrogen was added with continuous stirring hydroxy-guanidine hemisulphate hemihydrate (11.6 g, 0.086 mole) and powdered 4A molecular sieves (35 g) and the resulting slurry stirred at room temperature for 15 min. To this was added (±) ethyl 1-azabicyclo[3.2.1]oct-5-yl carboxylate (D3, 4 g, 0.0218 mole) and the reaction mixture heated under reflux for 5 h. The reaction mixture was then cooled and adjusted to pH 7 with glacial acetic acid, filtered and the filtrate concentrated in vacuo to a gum. This residue was partitioned between chloroform and saturated aqueous potassium carbonate solution. The organic phase was separated, dried over anhydrous sodium sulphate and concentrated in vacuo to a gum which rapidly crystallised. Recrystallisation from ethyl acetate/methanol 1:1 afforded the title compound (E2, 1.9 g, 45%) m.p. 197°–199° C. $^1$H NMR (d$^6$—DMSO)δ1.5 (1H, m), 1.7–2.25 (5H, m), 265–3.15 (6H, m) 5 85 (2H, s, NH$_2$) $^{13}$C NMR (d$^6$—DMSO)δ 18.7 (CH$_2$). 33.3 (CH$_2$). 35.45 (CH$_2$), 42.7 (C), 51.6 (CH$_2$), 53.6 (CH$_2$), 63.7 (CH$_2$), 168.3 (C), 180 9 (C).

EXAMPLE 3

(±) 5-(3-Acetylamino-1,2,4-oxadiazol-5-yl)-1azabicyclo[3.2.1]octane oxalate salt (E3)

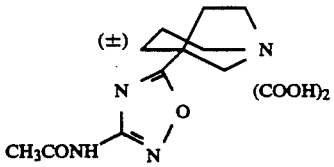

(E3)

A solution of (±) 5-(3-amino-1,2,4-oxadiazol-5-yl)-1-azabicyclo[3.2.1]octane (E2, 200 mg, 0.001 mole) in acetic anhydride (10 ml) was heated under reflux for 1h. The solvent was then removed in vacuo and the residue partitioned between chloroform and aqueous potassium carbonate solution. The organic phase was separated, dried over sodium sulphate and concentrated in vacuo to a gum. A solution of this in ether (20 ml) was treated with oxalic acid (100 mg) in methanol (1 ml) and the product which crystallised out recrystallised from methanol/ether to afford the title compound (E3, 80 mg, 25%). m.p. 177°–178° C.

Oxalate: ¹H NMR (d⁶—DMSO)δ2.0 (1H, m), 2.2 (3H, m), 2.25 (3H, s), 2.55 (2H, m), 3.4 (2H, m), 3.7 (4H, m), 11.35 (1H, s, N-H)

¹³C NMR (d⁶—DMSO)δ16.5 (4—C2), 23.2 (C3), 31.5 and 31.67 (3—C2, 6—C2), 42.6 (5-C), 49.7 and 51.3 and 58.8 (3×N—C2), 162.5 and 164.6 and 167.7 and 178.5 (3' and 5'—C, (CO₂H)₂, C=O).

EXAMPLE 4

4-(3-Amino-1,2,4-oxadiazol-5-yl)-1-azabicyclo 2.2.1]heptane (E4)

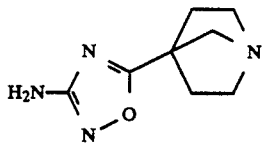

A stirred solution of sodium (950 mg, 0.041 mole) in dry ethanol (30 ml) at room temperature under nitrogen was treated with powdered 3A molecular sieves (10 g), hydroxy-guanidine hemisulphate hemihydrate (3.2 g, 0.024 mole) and ethyl 1-azabicyclo[2.2.1]hept-4-yl-carboxylate (D8, 1.0 g, 0.0059 mole) and the mixture heated under reflux for 4 h. The reaction mixture was allowed to cool to room temperature, then filtered and the filtrate concentrated in vacuo to leave a gum, which was treated with saturated potassium carbonate solution (30 ml) and extracted with chloroform (2×30 ml). The combined extracts were dried (Na₂SO₄) and concentrated in vacuo to give a gum, which was crystallised from methanol/ether to give the title compound (E4) as a white solid (330 mg, 31%) m.p. 225°-226° C.

¹H NMR (CD₃OD)δ1.72-1.85 (2H, m), 2.12-2.28 (2H, m), 2.70-2.87 (4H, m), 3.05-3.20 (2H, m). 13C NMR (CD₃OD)δ35.2 (CH₂), 47.9 (C), 55.2 (CH₂), 63.9 (CH₂), 169.0 (C), 179.7 (C).

EXAMPLE 5

4-(3-Fluoromethyl-1,2,4-oxadiazol-5-yl)-1-azabicyclo[2.2.1]heptane oxalate salt (E5)

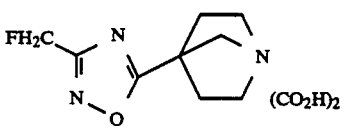

Ethyl 1-azabicyclo[2.2.1]hept-4-ylcarboxylate (D8, 1.03 g, 0.0061 mole) was treated with 8M hydrochloric acid (70 ml) and the solution heated under reflux for 12 h. The solution was concentrated in vacuo to leave a white solid, which was treated with thionyl chloride (50 ml) and heated under reflux for 4 h. The reaction mixture was concentrated in vacuo and the residue dissolved in ethanol-free chloroform (60 ml), treated with fluoroacetamide oxime (D1, 780 mg, 0.0080 mole) and heated under reflux for 3 h. The reaction mixture was basified with potassium carbonate solution and extracted with chloroform (2×50 ml). The combined extracts were dried (Na₂SO₄) and concentrated in vacuo to leave a beige solid, which was suspended in toluene (50 ml) and heated under reflux for 0.5 h. The mixture was concentrated in vacuo and the residue partitioned between saturated potassium carbonate solution and ethyl acetate. The organic solution was separated, dried (Na₂SO₄) and concentrated in vacuo to leave a yellow oil, which was chromatographed on basic alumina eluting with ether. The colourless oil obtained was converted to its oxalate salt and recrystallised from methanol/ether to give the title compound (E5) as a white solid (180 mg, 10%) m.p. 174°-176° C. Oxalate:- ¹H NMR (d⁶—DMSO)δ2.05-2.17 (2H, m), 2.28-2.45 (2H, m), 3.15-3.32 (2H, m), 3.35-3.52 (4H, m), 5.62 (2H, d, J=46 Hz).

BIOLOGICAL ACTIVITY

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO—M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 0.3H-QNB (Amersham International). For 3H—OXO—M, 1 ml of membranes is diluted to 6 ml and 0.1 ml mixed with test compound and 2nM (c. 250,000 cpm) 3H—OXO—M (New England Nuclear).

Non-specific binding of 3H—QNB is defined using 1 μM Atropine sulphate (2 μM Atropine) and of 3H—OXO—M using 10 μM Oxotremorine. Non-specific binding values typically are 5% and 25% of total binding, respectively. Incubations are carried out at 37° C. for 30 min and the samples filtered using Whatman GF/B filters. (In the 3H—OXO—M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC₅₀ values (i.e. the concentration which inhibits binding of the ligand by 50%) for the displacement of the muscarinic agonist 3H—OXO—M and the muscarinic antagonist 3H—QNB. The ratio IC₅₀(3H—QNB)/IC₅₀(3H—OXO—M) gives an indication of the agonist character of the compound. Agonists typically exhibit a large ratio; antagonists typically exhibit a ratio near to unity.

The results are shown in Table 1.

TABLE 1

| Compound | [³H]-OXO-M IC₅₀ (nM) | [³H]-QNB IC₅₀ (nM) |
| --- | --- | --- |
| E1 | 6.9 | 900 |
| E2 | 11.0 | 2000 |
| E4 | 32.5 | 2250 |
| E5 | 140.0 | 19500 |

We claim:

1. A compound of formula (I) or a pharmaceutically acceptable salt thereof:

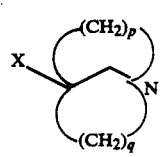

(I)

in which X represents a group

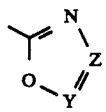

wherein one of Y and Z represents nitrogen and the other represents CR where R is selected from halogen, CN, $OR^1$, $SR^1$, $N(R^1)_2$, $NHR^1$, $NHCOR^1$, $NHCOOCH_3$, $NHCOOC_2H_5$, $NHNH_2$, $COR^1$, $COR^2$, $C_{2-4}$ alkenyl, $C_{2-4}$ alkynyl or $C_{1-2}$ alkyl substituted with $OR^1$, $N(R^1)_2$, $SR^1$, $CO_2R^1$, $CON(R^1)_2$ or one or two halogen atoms, in which $R^1$ is hydrogen or $C_{1-2}$ alkyl and $R^2$ is $OR^1$, $NH_2$ or $NHR^1$; and each of p and q independently represents an integer of 2 to 4.

2. A compound according to claim 1 in which X represents a group

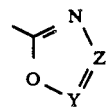

wherein Y is nitrogen and Z is CR where R is as defined in claim 1.

3. A compound according to claim 2 wherein R is selected from $NH_2$, $CH_2F$ and $NHCOCH_3$.

4. A compound according to claim 1 in which p represents 2 and q represents 2 or 3.

5. A compound selected from:

(±) 5-(3-fluoromethyl-1,2,4-oxadiazol-5-yl)-1-azabicyclo[3.2.1]octane;

(±) 5-(3-amino-1,2,4-oxadiazol-5-yl)-1-azabicyclo[3.2.1]octane;

(±) 5-(3-acetylamino-1,2,4-oxadiazol-5-yl)-1-azabicyclo[3.2.1]octane;

4-(3-amino-1,2,4-oxadiazol-5-yl)-1-azabicyclo[2.2.1]heptane; and 4-(3-fluoromethyl-1,2,4-oxadiazol-5-yl)-1-azabicyclo[2.2.1]heptane; or a pharmaceutically acceptable salt thereof.

6. A pharmaceutical composition comprising a compound of formula (I) or a pharmaceutically acceptable salt thereof, as defined in claim 1, and a pharmaceutically acceptable carrier.

7. A method of treatment and/or prophylaxis of dementia in mammals including humans, which comprises administering to the sufferer an effective amount of a compound of formula (I) or a pharmaceutically acceptable salt thereof, as defined in claim 1.

* * * * *

UNITED STATES PATENT AND TRADEMARK OFFICE
CERTIFICATE OF CORRECTION

PATENT NO. : 4,988,706
DATED : January 29, 1991
INVENTOR(S) : Michael Stewart Hadley, et al It is certified that error appears in the above-identified patent and that said Letters Patent is hereby corrected as shown below:

In claim 1, col. 13, line 24, before "$NHNH_2$" insert -- $NHOR^1$ --

In claim 6, col. 14, line 26, after "composition" insert -- for the treatment and/or prophylaxis of dementia --;

after "comprising" insert -- a pharmaceutically effective amount of --.

In claim 7, col. 14, line 31, delete "including humans".

Signed and Sealed this

Sixteenth Day of March, 1993

*Attest:*

STEPHEN G. KUNIN

*Attesting Officer*  Acting Commissioner of Patents and Trademarks